United States Patent
Segman

(10) Patent No.: US 7,728,873 B2
(45) Date of Patent: Jun. 1, 2010

(54) APPARATUS FOR OBTAINING AND ELECTRONICALLY INTERPRETING DIGITAL IMAGES OF LIQUIDS, SOLIDS AND COMBINATIONS ON LIQUIDS AND SOLIDS

(75) Inventor: Yoseg Segman, Zichron Yaacov (IL)

(73) Assignee: CNOGA Ltd, Zichron Yaakov (IL)

( * ) Notice: Subject to any disclaimer, the term of this patent is extended or adjusted under 35 U.S.C. 154(b) by 768 days.

(21) Appl. No.: 10/983,604

(22) Filed: Nov. 9, 2004

(65) Prior Publication Data

US 2006/0098113 A1     May 11, 2006

(51) Int. Cl.
*H04N 5/225* (2006.01)
*H04N 5/222* (2006.01)
*H04N 7/18* (2006.01)

(52) U.S. Cl. .................. 348/207.99; 348/370; 348/127; 348/131

(58) Field of Classification Search ................. 348/127, 348/370, 371, 131, 132; 382/142; 356/239.4–239.6
See application file for complete search history.

(56) References Cited

U.S. PATENT DOCUMENTS

| | | | |
|---|---|---|---|
| 4,555,798 A | | 11/1985 | Broadbent, Jr. et al. |
| 4,902,137 A | * | 2/1990 | Krieg et al. ............... 356/239.6 |
| 5,414,778 A | * | 5/1995 | Schwartz et al. ............ 382/142 |
| 5,438,417 A | * | 8/1995 | Busch et al. ................ 348/128 |
| 5,510,620 A | * | 4/1996 | Achter et al. ................ 356/337 |
| 5,791,345 A | * | 8/1998 | Ishihara et al. .............. 600/368 |
| 5,936,725 A | | 8/1999 | Pike et al. |
| 6,055,876 A | * | 5/2000 | Kato ....................... 250/223 B |
| 2003/0185707 A1 | * | 10/2003 | Iwaki et al. .................... 422/58 |
| 2004/0114035 A1 | | 6/2004 | White |

\* cited by examiner

*Primary Examiner*—Nhan T Tran
(74) *Attorney, Agent, or Firm*—Mark M. Friedman

(57) ABSTRACT

An apparatus for electronically obtaining and interpreting the closely focused digital image of a substance has a housing, a light generation source, an optical sensor, an electronic control/input/processing/storage/output unit a display, an optional printer and optional data output ports. The electronic control/input/processing/storage/output unit controls the light generation source, which generates light, which light diffused through and over the substance and is sensed and converted to electrical impulses by the optical sensor array, which collective electrical impulses represent the closely-focused digital image of the substance, which digital image can be interpreted to report the relative quality of the substance.

18 Claims, 2 Drawing Sheets

APPARATUS FOR OBTAINING AND ELECTRONICALLY INTERPRETING DIGITAL IMAGES OF LIQUIDS, SOLIDS AND COMBINATIONS ON LIQUIDS AND SOLIDS

FIELD AND BACKGROUND OF THE INVENTION

The present invention relates to an apparatus for obtaining and electronically interpreting closely-focused digital images of liquids, solids and combinations of liquids and solids (which are hereinafter referred to individually as "substance" or collectively as "substances") being subjected to controlled quantities and qualities of light shining through and over such substance. More particularly, but not exclusively, one detailed described embodiment of the present invention set forth herein and referred to as a container-receiving embodiment relates to obtaining and electronically interpreting closely-focused digital images of wine in a sealed wine bottle or blood in a test tube. In addition, another detailed described embodiment of the present invention set forth herein and referred to as a handheld embodiment relates to obtaining and electronically interpreting digital images of substances in open containers, pools and piles or blood in capillaries.

The relative quality of many liquid, solid and combination of liquid and solid substances can be interpreted from various optical characteristics of those substances. Various optical arrangements are known for measuring and analyzing the various optical characteristics of test samples, such as spectrophotometers. The prior art devices, however, are typically bulky, expensive, require a high degree of operator skill and expertise, and usually require opening the container of substance and placing a sample of the substance being assayed into a carrier that is then further processed, placed in the testing apparatus and tested. The present invention is designed to simply and economically capture a closely focused digital image of a substance while the substance is being subjected to a controlled light at various times during the manufacturing, transportation, sales, use and consumption cycle.

One use of the present invention is to obtain and store closely focused digital images of a substance at various stages of the manufacturing, transportation, sales, use and consumption cycle. By comparing the closely focused digital images obtained at the optimal stage of the manufacturing or packaging process and comparing the baseline digital images with subsequent digital images, one can detect differences in the digital images that indicate differences in the quality of the substance. In addition, one can program the electronic component of the present invention to ascertain and store distinct optical characteristics of a particular substance in a data table that correlates those distinct optical characteristics with other subjective sensory and other otherwise objectively measurable qualities of the substance in order to develop a correlative database that may be used to predict the "quality" of the substance based upon its distinct optical characteristics.

Many substances that are manufactured and sold in sealed transparent or translucent containers will degrade if the container and the substance contained therein are not properly cared for. Most of the prior art devices for testing whether the quality of a particular substance has been maintained require opening sealed containers of the substance for sampling and testing. For example, a consumer who wants to assess the quality of wine contained in a sealed bottle cannot presently do so without opening the bottle, which exposes the liquid contained therein to air containing both oxygen and aerobic bacteria, either one or both of which will promptly begin to act to degrade the wine. In addition, the need often arises to test the quality of substances contained in large bulk containers, vats, or natural land surface pools or piles in situations where obtaining a sample for use in a remote prior art device or transporting an unwieldy prior art device to the substance to be assayed is unfeasible. Finally, the prior art devices usually assay distinct optical characteristics, such as absorption of various light spectra or the presence of particular substances, which assays usually are performed using means requiring expensive equipment or expensive reagents. An economical alternative to the prior art testing means is to obtain a closely-focused digital image of a specific substance known to be in an "optimal" condition, interpreting that digital image and maintaining a database of such closely-focused digital images for comparison with subsequent digital images of the same substance obtained at later stages of sales and delivery cycle and prior to consumption in order to assure the continued quality of the substance.

There is thus a widely recognized need for, and it would be highly advantageous to have, an apparatus that would allow for obtaining and electronically interpreting the closely focused digital images of substances contained in sealed transparent containers, including but not limited to bottles of wine, without having to break the seal on such containers. In addition, there is also a widely recognized need for an economical and highly portable apparatus that can be used for obtaining and electronically interpreting the digital images of substances contained in large bulk liquid containers, vats, and open pools and piles. Finally, there is also a widely recognized need for a quality assurance mechanism for testing the optical characteristics of substances economically by obtaining and interpreting their digital images instead of other optical characteristics using prior art devices.

The aim of the present invention is to provide an improved apparatus which overcomes or substantially reduces at least some of the drawbacks and limitations of the prior art by allowing for obtaining and electronically interpreting a closely focused digital image of a substance at the time that the substance is being subjected to controlled qualities and quantities of light shining through and over the substance. The preferred embodiments of the present invention are capable of obtaining and interpreting such closely-focused digital images of substances contained in transparent containers, large bulk containers, vats and open pools or piles without having to open the containers or remove discrete samples of the fluids and solids being assayed.

SUMMARY OF THE INVENTION

According to the present invention there is provided an apparatus for obtaining and electronically interpreting closely-focused digital images of substances contained in sealed transparent containers, large bulk containers, vats, and open pools and piles, while the substances are being subjected to controlled qualities and quantities of light. The apparatus includes: a housing; a light generation source; a digital optical sensor array; an electronic device for inputting data to identify the liquid or solid, to set the quality and quantities of light to be allowed to be diffused through the liquid or over the solid, to receive the digital image from the optical sensor array, to store the digital image, to interpret the digital image, and to output data concerning the interpreted digital image; a data display and/or printer, and other data output ports. Different embodiments of the present invention will allow for testing substances in different types of containers or in large bulk containers, vats, and open pools and piles.

A container-receiving embodiment is suggested for obtaining and interpreting closely-focused digital images of substances contained in small, sealed, transparent containers, such as wine bottles. A second handheld embodiment is suggested for obtaining and interpreting digital images of substances in large bulk storage containers, vats, pools and piles.

More completely described, the housing for the container-receiving embodiment is a mechanism for positioning sealed transparent containers in the device. The housing also serves as a structure upon which to attach the other operative units of the device. For the container-receiving embodiment of the device for use with containers such as wine bottles, the housing would be constructed of an appropriate size and shape such that when a container is placed in the device, the light generating source and optical sensor array are in very close proximity to the container, such that the controlled light can illuminate the substance contained in the container and a closely-focused digital image can be obtained of the substance in the container being subjected to the light. For the handheld embodiment used to obtain closely-focused digital images of a substance contained in large bulk containers, vats, open pools and piles of various shapes and sizes, the housing would be constructed such that the light generation source and the optical sensor array can both be simultaneously placed in close proximity to the container, pool or pile of the substance such that the controlled light can illuminate the substance contained and a closely-focused digital image can be obtained of the substance at the same time that the substance is being illuminated by the light.

The light generation source for any embodiment of the device may be any light-generating source capable of producing a consistent continuous beam or timed flash of light. The light generated by the light generation source shines through and over the substance and illuminates the substance such that a closely-focused digital image the substance may be obtained at the précised time that the substance is being subjected to the controlled quality and quantity of light. The optical sensing array for any embodiment may be any type of optical sensing array capable of consistently converting the light shining through or over the substance into electrical impulses and transmitting the electrical impulses as digital images.

The light generation source may generate white light or a sequence of monochrome light (e.g. laser light) having certain wavelengths $\lambda 1, \lambda 2, \lambda 3 \ldots \lambda p$. The optical sensing array is designed to sense each of the light wavelengths shining through or over the substance under consideration. In case of white light the optical sensing array is designed to sense certain wavelengths shining through or over the material under consideration. For example, in case of measuring oxygen and/or glucose level in blood capillaries either by using white source light or a sequence of monochrome light, the oxygen in the blood is sensitive to light at wavelengths between 600 nm to 1200 nm and glucose is sensitive to wavelengths in range between 1500 nm to 3000 nm. Sensing the near visible infra red wavelengths is achieved by using a CCD sensor array without a glass filter in front of the array (such CCD's exists in several models of digital cameras) in order to increase the CCD sensitivity up to infra red range of 1200 nm. The device is designed to be generic with the ability to replace the light generation source and the optical sensor array so that it can capture a variety of sequences of digital images using different types of light generation sources and respective optical sensor arrays.

The captured sequence of images carries the information concerning the light shining through and over the substance being studied. Standard image processing and inverse problem techniques can be used to recognize the oxygen or glucose level of the captured images of the blood capillaries. The captured sequence of images is transferred into the memory unit and the CPU is designed to execute the embedded image processing software unit for analyzing the nature of the substance whether it is wine quality or oxygen or glucose level in capillaries or test tube. Standard image processing and inverse problem techniques can be used to recognize the oxygen or glucose level of the captured images of the blood capillaries. Standard methods of image processing for analyzing the captured images include but are not limited to local spatial-temporal Fourier and Wavelets analysis, pattern recognition, inverse methods and neural network methods.

The electronic unit serves as a mechanism for transmitting control data to the light generation source and receiving the electrical impulses as digital images from the optical sensor unit as data input, storing the raw data input, processing the data input, storing the processed data and outputting the processed data as processed data output.

The output data is displayed either textually or graphically on the data display unit or printer. Alternatively, the processed data output will be output to a variety of removable peripheral storage, display or printing devices.

The above and further features of the present invention are set forth in the appended claims and, together with some advantages thereof, will become more clear from consideration of the following detailed descriptions of exemplary embodiments of the invention given with reference to the accompanying drawings.

The present invention successfully addresses the shortcomings of the presently known configurations of prior art analysis devices. The present invention provides an apparatus into which, using the container-receiving embodiment, a pertinent part of a transparent container of substance needing to be assayed can be positioned or, in the case of using the handheld embodiment, large bulk liquid containers, vats, pools and piles of containers can be positioned in a manner such that light can be generated from the light generation source, shined through and over the substance and sensed by the optical sensor and some optical characteristics of such substance can thus be obtained as a closely-focused digital image, which closely-focused digital image can then be electronically interpreted without breaking the seal on the container or removing a representative sample from such bulk storage containers, vats, pools or pile of substance.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
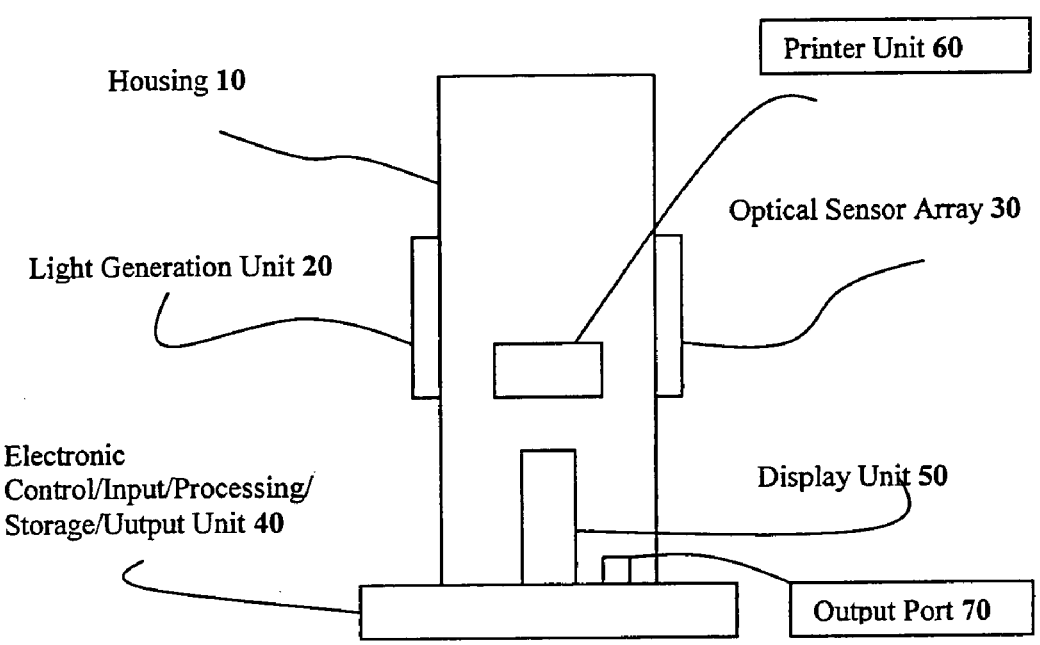
FIG. 1 is a schematic plan view of an exemplary container-receiving apparatus embodying the present invention for obtaining and interpreting a closely-focused digital image of a substance in a transparent container.

The present invention is of an apparatus that can be used for obtaining and interpreting the closely focused digital image of a substance contained in transparent containers or in large bulk containers, vats pools and piles. Specifically, but without limitation, the present invention can be used to obtain and interpret the closely focused digital image of wine contained in a sealed bottle or open vat. The principles and operation of some non-exclusive exemplary embodiments of such an apparatus for obtaining and interpreting the closely focused digital images of substances in containers according to the present invention may be better understood with reference to the drawings and the accompanying description.

In the case of the container-receiving embodiment 1 to be used for testing sealed containers of liquid that are of a size and shape allowing an appropriately sized and shaped container of liquid to be placed inside container-receiving embodiment, such a container is placed in the housing 10 in close proximity simultaneously to both the light generation source 20 and the optical sensory array 30. Control data is entered into an electronic control/input/processing/storage/output unit 40 selecting or inputting the definition of the substance to be assayed, and the quality and quantity of light to be generated and sensed. Light is generated by the light generation source 20, shines through the substance, and is sensed and converted to electrical impulses by the optical sensor array 30, which collective electrical impulses represent the closely-focused digital image of the substance. The closely-focused digital image is transmitted by the optical sensor array 30 to the electronic control/input/processing/storage/output unit 40 as raw data. The raw data is first stored by the electronic control/input/processing/storage/output unit 40 and then processed by the electronic control/input/processing/storage/output unit 40 and stored by the electronic control/input/processing/storage/output unit 40 as processed data. Next, the processed data is transmitted by the electronic control/input/processing/storage/output unit 40 as processed output data to one or more of a data display unit 50, printer 60, or data output ports 70.

In the case of the handheld embodiment used for testing large bulk containers, pools and piles of a substance which are not of a size or shape that they are able to be placed inside of the preceding container-receiving embodiment, the handheld apparatus is held in close proximity to and pointed at either the surface of the substance. Control data is entered into the electronic control/input/processing/storage/output unit 140 selecting the substance to be assayed, the type of container containing the substance and the quality and quantity of light to be generated and sensed. Light is generated by the light generation source 120, shines through and over the liquid, and is sensed and converted to electrical impulses by the optical sensor array 130, which collective electrical impulses represent the closely-focused digital image of the substance. The closely-focused digital image is transmitted by the optical sensor array 130 to the electronic control/input/processing/storage/output unit 140 0. The closely-focused digital image of the substance is stored as raw data. The raw data is processed by the electronic control/input/processing/storage/output unit 140 and stored by the electronic control/input/processing/storage/output unit 140 as processed data. The processed data is transmitted by the electronic control/input/processing/storage/output unit 140 as processed data output to one or more of a data display unit 150, a printer 160 or data output ports 170.

Referring now to the drawings, FIG. 1 illustrates the container-receiving embodiment of the present invention used as an apparatus for electronically obtaining and interpreting the closely focused digital image of a substance in a translucent containers, said apparatus including: a housing 10, a light generation source 20, an optical sensor array 30, an electronic control/input/processing/storage/output unit 40, a display unit 50, a printer unit 60, and one or more data output ports 70.

The housing 10 serves as a container receiver and positioner for holding containers of substance. The housing 10 is adapted with a container-receiving hole 11 in the top end of the housing 10 equal in size to the circumference of the housing 10, a light generation hole 12 located in the side of said housing 10 and a optical sensor hole 13 also located in the side of said housing 10. The light generation source 20 is a lamp, laser or any other light source attached to the housing 10 over the light generation hole 12 in a manner that allows light generated through the light generation hole 12 to shine through and over the container of substance to be assayed and the substance contained therein. The optical sensor array 30 is any type of optical sensor array including a charge-coupled device (CCD), a complementary metal oxide semiconductor (CMOS), ultraviolet, infrared, thermal or any other optical device that converts sensed light into electricity. The optical sensor array 30 is attached to the housing 10 over the optical sensing hole 13 in a manner such that the light generated by the light generation source 20 shines through the container of substance and the substance contained therein and the light is sensed through the optical sensing hole 13 by the optical sensory array 30 and converted to electrical impulses representing a closely focused digital image of the substance, which digital image is then transmitted.

The electronic control/input/processing/storage/output unit 40 is structurally attached to the housing 10 and electrically attached to the light generation unit 20 and the optical sensor array 30 such that the light generation may be controlled by the electronic control/input/processing/storage/output unit 40 and the digital image transmitted by the optical sensor array 30 may be received as raw data input into the electronic control/input/processing/storage/output unit 40. The raw data is be stored by electronic control/input/processing/storage/output unit 40, processed by the electronic control/input/processing/storage/output unit 40, stored by the electronic control/input/processing/storage/output unit 40 as processed data and output as processed data output in the form of a storable or viewable digital image.

The electronic control/input/processing/storage/output unit 40 is programmable to allow storage and comparison of digital images of particular empty containers and particular substances in at sequential points in time and to allow qualification and quantification of the optical characteristics of the substances expressed by the closely focused digital images for comparison with earlier or later closely focused digital images of the same substance or with different substances.

The display unit 50 is structurally attached to the housing 10 and electrically attached to the electronic control/input/processing/storage/output unit 40 such that the data processed and output by the electronic control/input/processing/storage/output unit 40 can be viewed by a user of the apparatus as textual or graphical output information. A printer unit 60 is structurally attached to the housing 10 and electrically attached to the electronic control/input/processing/storage/output unit 40 such that the data processed and output by the electronic control/input/processing/storage/output unit 40 can also be printed by a user of the apparatus as printed textual or graphical output information. One or more data output ports 70 including USB, RS232, infrared or any other communication output device can be structurally and electrically attached to the electronic control/input/processing/storage/output unit 40 such that the output data can be digitally stored or viewed by a user using any compatible removable storage, printing or display device.

Figure 2:
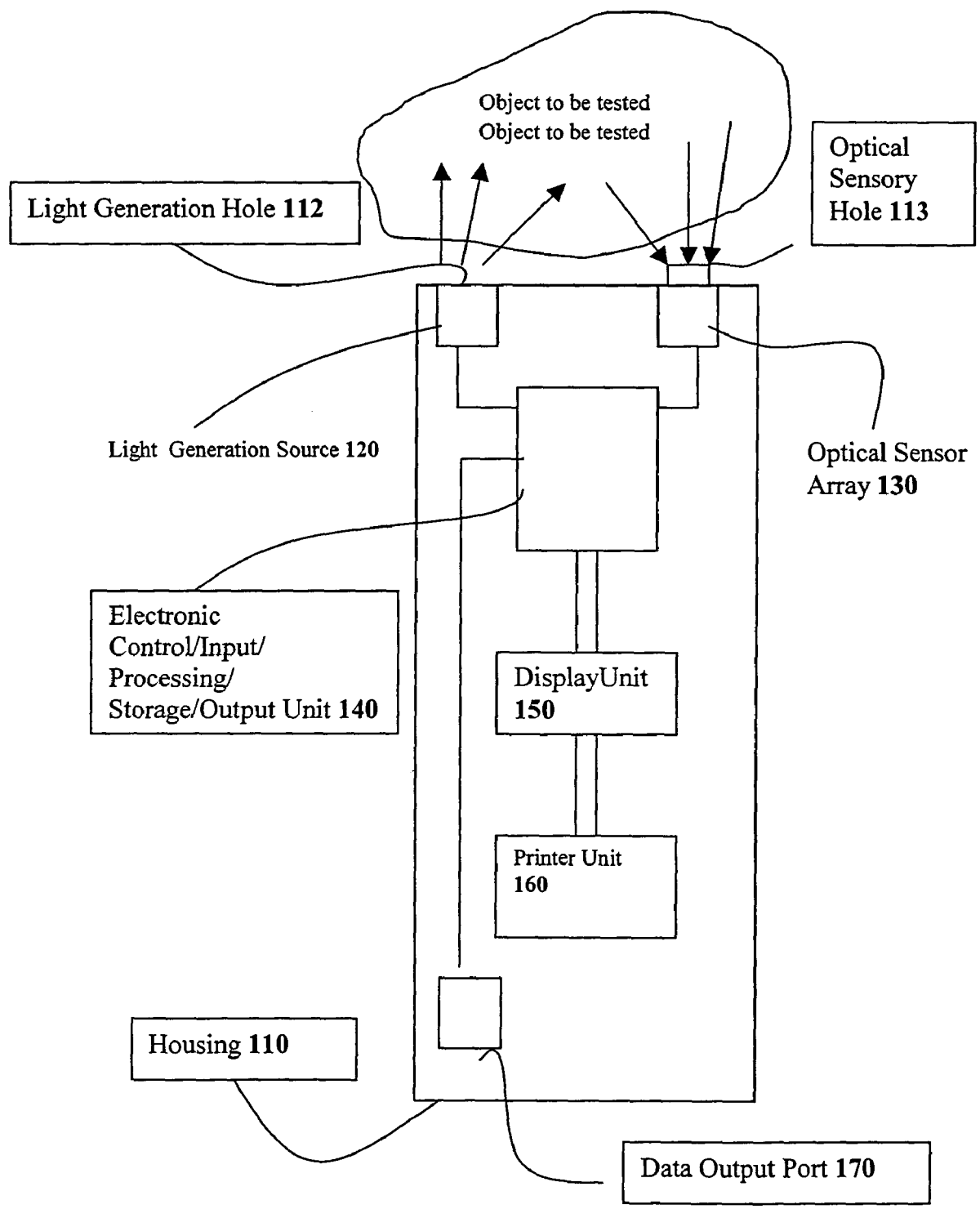
FIG. 2 is a schematic plan view of an exemplary handheld apparatus embodying the present invention for obtaining and interpreting a closely-focused digital image of substance in an open pile.

Another embodiment showing a configuration of the handheld embodiment is shown in FIG. 2, which illustrates an embodiment of the present invention used as an apparatus for electronically obtaining and interpreting the closely-focused digital image of a substance in large bulk containers, vat, pool or pile, said apparatus including: a, an optical sensory hole 113, a light generation source 120, an optical sensor array 130, an electronic control/input/processing/storage/output unit 140, a display unit 150, a printer unit 160, and data output ports 170.

The housing 110 is adapted with a light generation hole 112 and an optical sensory hole 113. The light generation source 120 uses a lamp, laser or any other light source attached across the light generation hole 112 of the housing 110 in a manner that light may be generated through the light generation hole 112, diffuse through a translucent section of the container or an exposed area of the substance to be assayed, and be sensed through the optical sensory hole 130 by the optical sensor array 140. The optical sensor array 140 can be a charge-coupled device (CCD), complementary metal oxide semiconductor (CMOS), ultraviolet, infrared, thermal or any other optical device that converts sensed light into electrical impulses, which collective electrical impulses represent the closely focused digital image of the liquid.

The electronic control/input/processing/storage/output unit 140 is structurally attached to the housing 110 and electrically attached to the light generation source 120 and the optical sensor array 130 such that the light generation may be controlled by the electronic control/input/processing/storage/output unit 140 and the digital image transmitted by the optical sensor array 130 may be received as raw data input into the electronic control/input/processing/storage/output unit 140. The raw data is stored as raw data by the electronic control/input/processing/storage/output unit 140, processed by the electronic control/input/processing/storage/output unit 140, stored by the electronic control/input/processing/storage/output unit 140 as processed data and output as processed data output in the form of a output digital image or process output data of such digital image.

The display unit 150 is structurally attached to the housing 110 and electrically attached to electronic control/input/processing/storage/output unit 140 such that the output data processed and output by electronic control/input/processing/storage/output unit 140 can be viewed by a user of the apparatus as textual or graphical output information. A printer unit 160 is structurally attached to the housing 110 and electrically attached to the electronic control/input/processing/storage/output unit 140 such that the data processed and output by the electronic control/input/processing/storage/output unit 140 can also be printed by a user of the apparatus as printed textual or graphical output information. Data output ports 170 including one or more of USB, RS232, infrared or any other communication output device are attached structurally to the housing 110 and electrically to the electronic control/input/processing/storage/output unit 140 such that said output data can be digitally stored or viewed by a user using any removable compatible storage, printing or display device.

While the invention has been described with respect to a limited number of embodiments, it will be appreciated that many variations, modifications and other applications of the invention may be made.

What is claimed is:

1. A method of evaluating a quality of a liquid by a consumer of that liquid, the method comprising:
    a) shining a continuous spectrum of light through said liquid located within a sealed container such that said continuous spectrum of light:
        (i) enters into said container;
        (ii) traverses said liquid within said container; and
        (iii) exits said container; and
    b) using an optical sensor array in close proximity to said container, receiving said container-exiting continuous spectrum of light of step (a), the optical sensor array not forming part of a human being;
    c) generating, from said received continuous spectrum of light, a closely focused image of said liquid;
    d) obtaining other subjective sensory evaluation of a quality of level of the liquid from other sensory perception of the liquid;
    e) correlating distinct optical characteristics obtained from the closely focused image with the quality level from the other subjective sensory evaluation and storing the correlation in a database;
    f) repeating steps (a) through (c) at a later time to form a new closely focused image of the liquid;
    g) obtaining distinct optical characteristics of the new closely formed image of the liquid; and
    h) predicting the quality of the liquid from the distinct optical characteristics of the new closely focused image of the liquid by using the database.

2. The method of claim 1 further comprising:
    i) positioning a light generation source capable of generating said continuous spectrum of light in close proximity to said container at a time that said optical sensor array is also in close proximity to said container; and
    j) using said light generating source, generating said continuous spectrum light which subsequently, in step (a), shines through said liquid within said container.

3. The method of claim 1 wherein:
    i) said optical sensor array resides in a device housing together with a light generation source capable of generating said continuous spectrum of light; and
    ii) the method further comprises:
        e) positioning said liquid-containing container within said device housing such that both said optical sensor array and said light generation source are simultaneously in close proximity with said liquid-containing container; and
        f) using said light generating source, generating said continuous spectrum of light which subsequently, in step (a), shines through said liquid within said container.

4. The method of claim 1 wherein said liquid is blood and said chemical concentration within the blood is also determined from the closely focused image.

5. The method of claim 1 wherein said liquid is a beverage.

6. The method of claim 1 wherein said liquid is an alcoholic beverage.

7. The method of claim 1 wherein said liquid is a wine.

8. The method of claim 1 wherein said continuous spectrum of light includes white light.

9. A method of evaluating a quality of a liquid by a consumer of that liquid, the method comprising:
    a) providing a liquid located within a sealed container;
    b) providing a device including:
        i) a housing;
        ii) light generation source capable of generating a continuous spectrum of incoherent light; and
        iii) an optical sensor array, said light generation source and said optical sensor array residing together in said housing, the optical sensor array not forming part of a human being;
    c) simultaneously positioning said light generation source and said optical sensor array in close proximity of said container;
    d) using said light generation source, generating continuous spectrum of light such that said incoherent light:

i) enters into said container;
ii) reflects from said liquid within said container;
iii) exits said container;
e) receiving with said optical sensor array in close proximity to said container said reflected continuous spectrum of light; and
f) generating from said received continuous spectrum of light an image of said liquid;
g) obtaining other subjective sensory evaluation of a quality level of the liquid from other sensory perception of the liquid;
h) correlating distinct optical characteristics obtained from the image with the quality level from the other subjective sensory evaluation and storing the correlation in a database;
i) repeating steps (a) through (c) at a later time to form a new closely focused image of the liquid;
j) obtaining distinct optical characteristics of the new closely formed image of the liquid; and
k) predicting the quality of the liquid from the distinct optical characteristics of the new closely focused image of the liquid by using the database.

10. The method of claim 9 wherein said optical sensor array and said light source are next to each other within said housing.

11. The method of claim 9 further comprising determining a chemical composition within the liquid.

12. The method of claim 9 wherein said liquid is a beverage.

13. The method of claim 9 wherein said liquid is an alcoholic beverage.

14. The method of claim 9 wherein said liquid is a wine.

15. The method of claim 9 wherein said continuous spectrum of light includes white light.

16. The method of claim 9
wherein the image is a closely focused image and distinct optical characteristics are spatial-temporal inhomogeneities within said closely focused image and wherein the method further comprises determining a chemical concentration within said liquid.

17. The method of claim 16 wherein said analyzing of said temporal-spatial inhomogeneities includes effecting at least one of spatial-temporal Fourier analysis and spatial Wavelets analysis of said closely focused image.

18. A method for generating an image, the method comprising:
a) providing a liquid located within a container;
b) allowing a continuous spectrum of light to shine through said liquid within said container such that said continuous spectrum of light:
(i) enters into said container;
(ii) traverses said liquid within said container; and
(iii) exits said container; and
c) using an optical sensor array not forming part of a human being in close proximity to said container, receiving said container-exiting continuous spectrum, of light of step (b);
d) generating, from said received continuous spectrum of light, a closely focused image of said liquid;
e) obtaining other subjective sensory evaluation of a quality level of the liquid from other sensory perception of the liquid;
f) correlating distinct optical characteristics obtained from the closely focused image with the quality level from the other subjective sensory evaluation and storing the correlation in a database;
g) subjecting said generated closely focused image to at least one of spatial-temporal Fourier analysis and spatial-temporal Wavelets analysis; and
h) in accordance with results of said spatial-temporal Fourier and/or Wavelets analysis, determining from said closely focused image a chemical concentration within said liquid.

* * * * *